United States Patent
Takasu et al.

(10) Patent No.: US 11,143,595 B2
(45) Date of Patent: Oct. 12, 2021

(54) PLASMA SPECTROSCOPY ANALYSIS METHOD

(71) Applicant: ARKRAY, Inc., Kyoto (JP)

(72) Inventors: Tsuyoshi Takasu, Kyoto (JP); Kojiro Honma, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 301 days.

(21) Appl. No.: 16/390,513

(22) Filed: Apr. 22, 2019

(65) Prior Publication Data
US 2019/0331606 A1 Oct. 31, 2019

(30) Foreign Application Priority Data
Apr. 26, 2018 (JP) .............................. JP2018-085538

(51) Int. Cl.
*G01N 21/67* (2006.01)
*G01N 21/66* (2006.01)
*G01N 21/69* (2006.01)
*G01N 33/493* (2006.01)

(52) U.S. Cl.
CPC .......... *G01N 21/67* (2013.01); *G01N 33/493* (2013.01); *G01N 21/66* (2013.01); *G01N 21/69* (2013.01)

(58) Field of Classification Search
CPC .... G01N 21/20; G01N 21/64; G01N 21/6428; G01N 21/66; G01N 21/67; G01N 21/69; G01N 33/493
USPC ..... 436/73, 74, 77, 149, 150, 151, 164, 172, 436/63
See application file for complete search history.

(56) References Cited

U.S. PATENT DOCUMENTS

| | | | |
|---|---|---|---|
| 5,368,707 A * | 11/1994 | Henkens | C12Q 1/003 204/403.14 |
| 8,765,480 B2 * | 7/2014 | Shimomura | G01N 1/4044 436/73 |
| 9,873,925 B2 * | 1/2018 | Shimomura | C22B 7/006 |
| 10,295,471 B2 * | 5/2019 | Kasai | G01N 21/69 |
| 10,539,548 B2 * | 1/2020 | Kiriyama | G01N 1/38 |
| 10,551,323 B2 * | 2/2020 | Honma | G01N 21/67 |
| 2016/0202187 A1 * | 7/2016 | Shiraki | G01N 21/67 356/316 |
| 2018/0024069 A1 * | 1/2018 | Takasu | G01N 21/73 356/316 |

(Continued)

FOREIGN PATENT DOCUMENTS

| | | |
|---|---|---|
| JP | 2016-130734 A | 7/2016 |
| JP | 2018-021902 A | 2/2018 |

OTHER PUBLICATIONS

The extended European search report issued by the European Patent Office dated Aug. 12, 2019, which corresponds to EP19170953.4-1020 and is related to U.S. Appl. No. 16/390,513.

*Primary Examiner* — Maureen Wallenhorst
(74) *Attorney, Agent, or Firm* — Studebaker & Brackett PC

(57) ABSTRACT

A plasma spectroscopy analysis method includes a preliminary addition process in which a bonding agent that is an agent other than DMSA is added to the specimen collected from a living body to which meso-2,3-dimercaptosuccinic acid (DMSA) is administered, a concentration process in which the analyte heavy metal ions in the specimen at a vicinity of one of a pair of electrodes by applying a voltage to the pair of electrodes, and a detection process in which plasma is generated by applying a voltage to the pair of electrodes, and luminescence of the analyte metal ions caused by the plasma is detected.

1 Claim, 6 Drawing Sheets

(56) References Cited

U.S. PATENT DOCUMENTS

2018/0230608 A1\* 8/2018 Kasai .................. G01N 21/67

\* cited by examiner

PLASMA SPECTROSCOPY ANALYSIS METHOD

CROSS-REFERENCE TO RELATED APPLICATION

This application claims priority under 35 USC 119 from Japanese Patent Application No. 2018-085538, filed on Apr. 26, 2018, the disclosure of which is incorporated by reference herein.

BACKGROUND

Technical Field

The present disclosure relates to a plasma spectroscopy analysis method.

Related Art

JP 2016-130734 A reports a plasma spectroscopy analysis method that includes: a process of applying a voltage to a pair of electrodes disposed in a sample to concentrate an analyte; and a detection process of similarly applying a voltage to generate plasma and detecting luminescence of the analyte that is caused by the plasma. More specifically, a method is disclosed of continuing to concentrate metal ions in a specimen at an electrode by stripping, passing a large current between the electrodes to cause plasma luminescence from the metal ions, and quantifying metal ions in the specimen from luminescence amounts.

To remove heavy metals that have accumulated in a living body, a therapy of administering a chelating agent to a patient to promote the excretion of metal ions (chelation) has been established. In order to verify the efficacy of this therapy, a specimen (for example, urine) is collected from the patient after the administration of the chelating agent, and heavy metal ions contained in the specimen are measured. At this time, certain substances that are excreted in urine due to effects of the chelating agent (co-substances) may influence the measurement of the metal ions. Specifically, a measured concentration of metal ions in a specimen may be lower than the actual concentration.

In order to reduce the influence of these co-substances, a method such as that in JP 2018-21902 A is effective: in the concentration process of the plasma spectroscopy analysis method, the current that flows for concentration is periodically switched on and off. Electron transfers associated with the concentration are kept constant in the concentration step by the current flowing between the electrodes being controlled to be constant when the current is on. Consequently, it is reported that it is possible to reduce errors caused by conditions of the specimen such as, for example, the presence of co-substances.

In the plasma spectroscopy analysis method described above, when meso-2,3-dimercaptosuccinic acid (DMSA) is administered to a patient as the chelating agent and metal ions in urine from the patient are measured, the measurement sensitivity of particular metal ions (for example, lead ions) may be lower, and measurement may not be possible.

SUMMARY

The present disclosure enables accurate measurement by a plasma spectroscopy analysis method of particular metal ions such as, for example, lead ions in a specimen collected after administration of DMSA.

A plasma spectroscopy analysis method according to the present disclosure includes: a preliminary addition process including adding a bonding agent which is capable of bonding with analyte heavy metal ions to a specimen collected from a living body to which meso-2,3-dimercaptosuccinic acid (DMSA) is administered, and the bonding agent being an agent other than DMSA; a concentration process including concentrating the analyte heavy metal ions in the specimen at a vicinity of one of a pair of electrodes by applying a voltage to the pair of electrodes; and a detection process including generating plasma by applying a voltage to the pair of electrodes, and detecting luminescence of the analyte heavy metal ions caused by the plasma.

The plasma spectroscopy analysis method of the present disclosure enables accurate measurement of particular metal ions such as, for example, lead ions in a specimen collected after administration of DMSA as a chelating agent, without sensitivity being lowered.

BRIEF DESCRIPTION OF THE DRAWINGS

Exemplary embodiments will be described in detail based on the following figures, wherein.

DETAILED DESCRIPTION

Figure 1A:
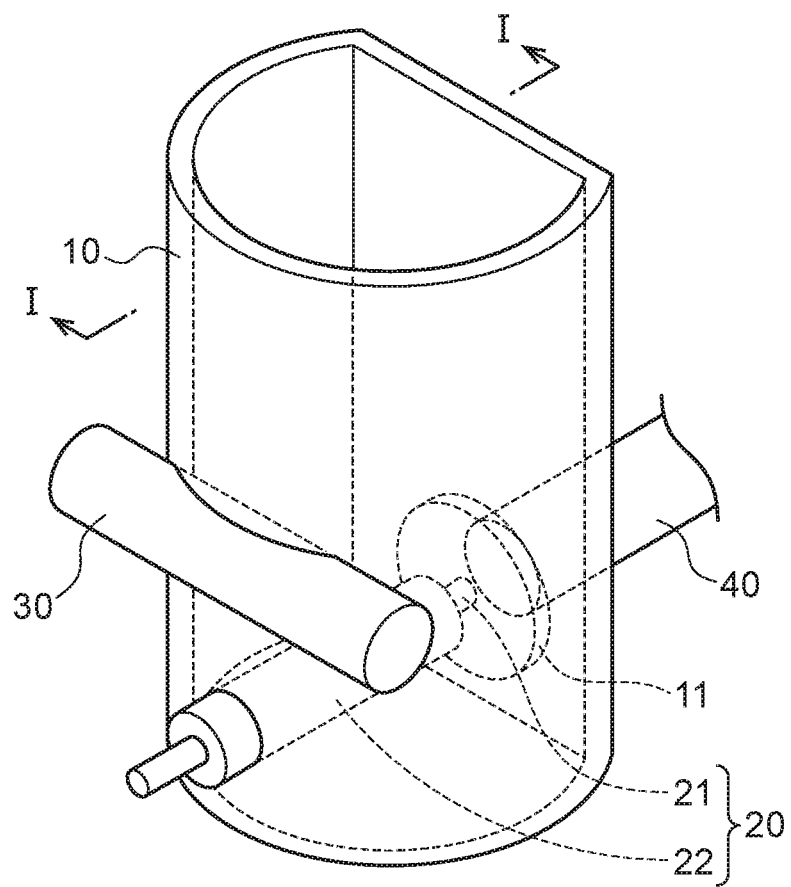
FIG. 1A is a schematic see-through perspective view of relevant portions of a measuring container employed in a present exemplary embodiment.

The plasma spectroscopy analysis method according to the present disclosure includes: a preliminary addition process including adding an auxiliary chelating agent to a specimen collected from a living body to which meso-2,3-dimercaptosuccinic acid (DMSA) is administered, and the auxiliary chelating agent being a chelating agent other than DMSA; a concentration process including, after the specimen to which the auxiliary chelating agent has been added has been introduced into a measuring container in which a pair of electrodes are disposed, concentrating the analyte heavy metal ions in the specimen at a vicinity of one of the electrodes by applying a voltage to the pair of electrodes; and a detection process including, after the concentration process, generating plasma by applying a voltage to the pair of electrodes, and detecting luminescence of the analyte heavy metal ions caused by the plasma.

The plasma spectroscopy analysis method according to the present aspect mentioned herein means: applying a predetermined voltage (stripping) between a pair of electrodes disposed in a measuring container into which a specimen has been introduced; and, after analyte heavy metal ions have been concentrated in a vicinity of one of the electrodes, applying a voltage such that, for example, a larger current flows than during the stripping, thus causing plasma luminescence from the concentrated analyte heavy metal ions, and quantifying the analyte heavy metal ions from luminescence amounts of the plasma luminescence.

The specimen mentioned herein, which is the object of measurement in this system, means a specimen from a living body. The characteristics and origin of the specimen are not particularly limited as long as the specimen is in a liquid state at the time of measurement. The specimen may be an undiluted solution of a liquid submitted for measurement or may be a dilute solution in which a liquid submitted for measurement is suspended, dispersed or dissolved in a liquid medium. Further, the specimen may be a dilute solution in which a solid submitted for measurement is suspended, dispersed or dissolved in a liquid medium, and the specimen may be a dilute solution in which a gas submitted for measurement is suspended, dispersed or dissolved in a liquid medium. So long as the liquid medium is able to suspend, disperse, or dissolve the specimen, there are no particular limitations to the liquid medium, and examples of the medium include water and buffers. As mentioned above, the specimen is a liquid or solid taken from a living body. Examples of a liquid or solid taken from a living body include urine, blood, saliva, sweat, hair, skin, tissue, nails, and the like; urine is desirable. Examples of the living body include a human or a non-human animal, specifically a patient or an animal under treatment.

Examples of the analyte heavy metal include metal ions of arsenic (As), bismuth (Bi), cadmium (Cd), lead (Pb), mercury (Hg), nickel (Ni), palladium (Pd), platinum (Pt), tellurium (Te), thallium (Tl), thorium (Th), tin (Sn), tungsten (W), and uranium (U); lead ions are desirable.

The specimen is a specimen collected after DMSA has been administered to the living body as a chelating agent. When, for example, ethylenediaminetetraacetic acid (EDTA) is administered to a patient as a chelating agent in order to cause excretion of metals in the body, the EDTA is infused by intravenous drip, which takes time. In contrast, DMSA as a chelating agent may be orally administered, and therefore is easier to use.

When, for example, DMSA is orally administered, the excretion of metal ions in urine is stimulated over the following 24 hours. In particular, the excretion of metal ions in urine is strongly stimulated over the six hours after oral administration. Accordingly, urine from the 24 hours after oral administration, particularly urine from the six hours after oral administration, is usually supplied as specimens for measurements to verify the efficacy of chelation after DMSA administration.

However, it may not be possible to accurately detect analyte heavy metal ions, particularly lead ions, in specimens collected after DMSA administration, particularly urine specimens. To be specific, it may not be possible to accurately detect analyte heavy metal ions, particularly lead ions, at least in urine specimens excreted from the body in the six hours after DMSA administration. The reasons for this are currently unclear, but there is speculation that particular components included in specimens collected after DMSA administration have some effect on lead ions in the concentration process and the detection process. Examples of these particular components are surmised to include DMSA itself, metabolites of DMSA, and components whose excretion from the body is induced by the side effects of DMSA. However, it is unclear whether these particular components are actually included in specimens. Even when the particular components are included, it is unclear whether or not lead ions bond or adsorb thereto.

In the preliminary addition process, an auxiliary chelating agent, which is a chelating agent other than DMSA, is added to the specimen. As the auxiliary chelating agent, for example, citric acid or EDTA may be used, and EDTA in particular may be preferably used. When an auxiliary chelating agent (particularly EDTA) is added to a specimen collected after the administration of DMSA, analyte heavy metal ions (particularly lead ions) may be measured accurately. Although the reasons why measurement is facilitated by this addition of EDTA are unclear, it is surmised that the cause is that EDTA has the characteristic of bonding with lead ions. Note that an "auxiliary chelating agent" mentioned in this disclosure is also referred to as a "bonding agent", in order to distinguish the auxiliary chelating agent (or the bonding agent) that is added to a specimen from a chelating agent that is administered to a living body used in a chelation therapy. The "bonding agent" has a nature being capable of chemically bonding with the analyte heavy metal ions. The bonding agent has at least one functional group to bond with the analyte heavy metal ion via a coordination bond, an ionic bond, a covalent bond and the like. It is preferable for the bonding agent to be a compound having a plurality of coordination positions that coordinate with an analyte heavy metal ion, and to bond with the analyte heavy metal ion via the coordination bond to form a metal complex. That is, it is preferable for the bonding agent to be a compound having an chelate effect to the analyte heavy metal ion.

The pH of a urine specimen may be adjusted before or after the preliminary addition process. The pH in such cases is not particularly limited so long as it is a pH that is conducive to detection of mercury or lead. The pH of the urine specimen can, for example, be regulated by a pH-regulating reagent that is an alkaline reagent, an acid reagent, or the like.

Examples of the alkaline reagent include alkalis and aqueous solutions of alkalis. Alkalis are not particularly limited, and examples include sodium hydroxide, lithium hydroxide, potassium hydroxide, and ammonia. Examples of aqueous solutions of alkalis include aqueous solutions in which alkali is diluted by water or a buffer. The concentration of the alkali in an aqueous solution is not particularly limited, and may, for example, be from 0.01 mol/L to 5 mol/L.

Examples of the acid reagent include acids and aqueous solutions of acids. Acids are not particularly limited, and examples include hydrochloric acid, sulfuric acid, acetic acid, boric acid, phosphoric acid, citric acid, malic acid, succinic acid, and nitric acid. Examples of aqueous solutions of acids include aqueous solutions in which acid is diluted by water or a buffer. The concentration of the acid in an aqueous solution is not particularly limited, and may, for example, be from 0.01 mol/L to 5 mol/L.

The concentration process mentioned herein means a process subsequent to the preliminary addition process in which the specimen is introduced into the measuring container and a voltage is applied to the pair of electrodes disposed in the measuring container, as a result of which analyte heavy metal ions in the urine specimen concentrate in a vicinity of one of the electrodes.

The pair of electrodes mentioned herein means a combination of an anode and cathode for electrolysis. The electrodes are solid electrodes, and specific examples thereof include rod electrodes. The material of the electrodes is not particularly limited, and as long as the material is a solid, conductive material, the material can be appropriately set according to, for example, the type of analyte heavy metal ions. The material of the electrodes may, for example, be a non-metal, may be a metal, or may be a mixture thereof. When the material of the electrodes includes a non-metal, then the material of the electrodes may, for example, include one type of non-metal, or may include two or more types of non-metal. Examples of the non-metal include carbon. When the material of the electrodes includes a metal, the material of the electrodes may, for example, include one type of metal, or may include two or more types of metal. Examples of the metal include gold, platinum, copper, zinc, tin, nickel, palladium, titanium, molybdenum, chromium, and iron. When the material of the electrodes includes two or more types of metal, the material of the electrodes may be an alloy. Examples of the alloy include brass, steel, INCONEL (registered trademark), nichrome, and stainless steel. The pair of electrodes may, for example, be the same material or may be different materials.

The sizes of the electrodes are not particularly limited as long as at least a portion of each can be accommodated in the measuring container. Note that in cases in which the measuring container is, for example, to be made into a cartridge to enable mass production, the size of the measuring container is preferably made as small as possible. In these cases, the electrodes should also be made smaller in accordance with the size of the measuring container. One or both of the pair of electrodes may be provided as a unit equipped to the measuring container beforehand, and one or both of the pair of electrodes may be inserted into the measuring container as appropriate at the time of measurement.

The one of the electrodes mentioned herein means the electrode at which the analyte heavy metal ions are concentrated. In this exemplary embodiment, this electrode is the cathode.

The concentration of analyte heavy metal ions may be regulated by, for example, the voltage. Thus, the voltage to generate the concentration (referred to as a "concentration voltage" hereinafter) can be appropriately set by a person of ordinary skill in the art. The concentration voltage is, for example, 1 mV or more, and is preferably 400 mV or more. The upper limit of the concentration voltage is not particularly limited. The concentration voltage may be fixed, or may fluctuate, for example.

The duration over which the concentration voltage is applied is not particularly limited, and may be appropriately set according to the concentration voltage. The duration of concentration voltage application is, for example, from 0.2 minutes to 40 minutes, and is preferably from 5 minutes to 20 minutes. The voltage applied across the pair of electrodes may, for example, be applied continuously, or may be applied intermittently. An example of the intermittent application is pulse application. In cases in which the concentration voltage application is intermittent, the duration of concentration voltage application may, for example, be a total duration only of times for which the concentration voltage is applied, or may be a total duration of times for which the concentration voltage is applied and times for which the concentration voltage is not applied.

A voltage application device serving as a device that applies the voltage across the pair of electrodes is not particularly limited. Any known device such as a voltage source may be employed therefor as long as it is capable of applying a voltage across the pair of electrodes. In the concentration process, the current flowing between the pair of electrodes may, for example, be set to 0.01 mA to 200 mA, is preferably set to 10 mA to 60 mA, and is more preferably set to 10 mA to 40 mA.

In the detection process, as stated above, plasma is generated by, for example, applying a voltage so as to produce a larger current across the pair of electrodes than during the concentration process, and luminescence of the analyte heavy metal ions caused by the plasma is detected.

The direction of the current in the detection process may be the same as the direction of the current in the concentration process. However, the voltage application device is preferably configured so as to be capable of switching the direction of current when applying voltage, and the direction of the current when generating plasma is preferably the opposite direction to the direction of current during the concentration process.

More specifically, in the concentration process, analyte heavy metal ions that have positive charges are concentrated in the vicinity of the one of the electrodes acting as the cathode, and in the detection process, the current direction from the voltage application device may be set such that this one electrode acts as the anode.

The detection process may be performed so as to be contiguous to the concentration process, or may be non-contiguous thereto. The detection process of the former case is a detection process performed as soon as the concentration process ends. The detection process of the latter case is a detection process performed within a predetermined time from when the concentration process ends. The predetermined time is, for example, from 0.001 seconds to 1000 seconds after the concentration process, and is preferably from 1 second to 10 seconds thereafter.

In the detection process, "generating plasma" mentioned herein means generating plasma to a practical level, and more specifically, with regard to detection of plasma luminescence, means causing plasma to be generated that produces a practically detectable level of luminescence. As a specific example, this may be said to be a level at which plasma luminescence is detectable by a plasma luminescence detector.

The generation of plasma at a practical level can be adjusted by, for example, the voltage. Thus the voltage to cause plasma to be generated so as to give a practically detectable luminescence (also referred to as the "plasma generation voltage" hereinafter) can be appropriately set by a person of ordinary skill in the art. The plasma generation voltage is, for example, 10 V or greater, and is preferably 100 V or greater. There is no particular limitation to the upper limit thereof. The plasma generation voltage is, for example, a relatively high voltage compared to the voltage used to cause the concentration. Thus, the plasma generation voltage is preferably a higher voltage than the concentration voltage. The plasma generation voltage may be fixed, or may fluctuate, for example.

The duration over which the plasma generation voltage is applied is not particularly limited, and may be appropriately set according to the plasma generation voltage. The duration over which the plasma generation voltage is applied may, for example, be from 0.001 seconds to 0.02 seconds, and is preferably from 0.001 seconds to 0.01 seconds. The plasma generation voltage across the pair of electrodes may, for example, be applied continuously, or may be applied intermittently. An example of the intermittent application is pulse application. In cases in which the plasma generation voltage application is intermittent, the duration of plasma generation voltage application may, for example, be the duration of one cycle of the plasma generation voltage application, may be the total duration of times for which the plasma generation voltage is applied, or may be the total duration of times for which the plasma generation voltage is applied and times for which the plasma generation voltage is not applied.

In the detection process, the luminescence of the generated plasma may be detected continuously or may be detected intermittently, for example. Examples of the luminescence detection include detection of the presence or absence of luminescence, detection of the intensity of the luminescence, detection of a particular wavelength, and detection of a spectrum. Examples of the detection of a particular wavelength include, for example, detection of a characteristic wavelength emitted by the analyte heavy metal ions during plasma luminescence. The method of detecting luminescence is not particularly limited and, for example, a known optical measurement instrument such as a charge coupled device (CCD) or a spectroscopy instrument may be utilized therefor.

The plasma generation voltage application across the pair of electrodes in the detection process is performed by the voltage application device employed in the concentration process, and can be performed at a higher voltage and preferably with the current direction in the opposite direction. Because the plasma generation voltage is higher than the concentration voltage, the current between the electrodes in the detection process is larger than in the concentration process. The current in the detection process is, for example, set to 0.01 mA to 100,000 mA, and is preferably set to 50 mA to 2000 mA.

A luminescence spectrum obtained from the plasma luminescence in the detection process may be depicted as a graph in which luminescence amounts for separate wavelengths are plotted over a predetermined wavelength range. A net luminescence amount corresponding to an analysis wavelength, which is a wavelength applicable to quantifying the analyte heavy metal ions, is preferably found from this luminescence spectrum.

The net luminescence amount mentioned herein means a luminescence amount at the analysis wavelength that is caused only by the presence of the analyte heavy metal ions. This means a luminescence amount obtained by correcting the luminescence amount observed at the analysis wavelength by a base luminescence amount, which is a luminescence amount unrelated to plasma luminescence from the analyte heavy metal ions. Net luminescence amount values are referred to as corrected light amount values.

A method of determining or calculating a base luminescence amount may be appropriately set depending on what kind of graph is obtained as the luminescence spectrum. For example, if a peak luminescence amount corresponding to a particular wavelength is obtained in the form of a region rising from a flat region of the graph of the luminescence spectrum, a luminescence amount of the flat region may be set as the base luminescence amount.

An example of the measuring container employed in the present exemplary embodiment is described with reference to the drawings. In these figures, the structure of each section may be simplified as appropriate for explanation and illustrated schematically, such that the proportions and so on of each section differ from their actual proportions.

Figure 1B:
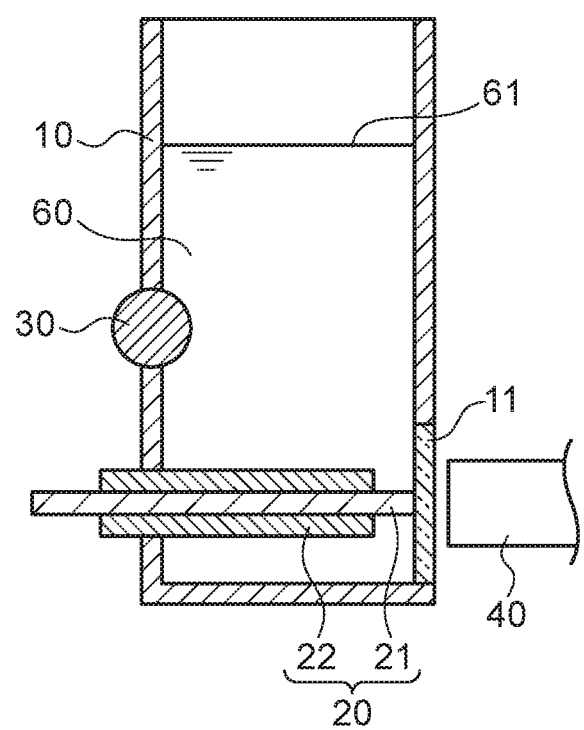
FIG. 1B is a schematic sectional diagram of FIG. 1A, taken along line I-I.

FIG. 1A is a schematic see-through perspective view of relevant portions of a measuring container 10 employed in the present exemplary embodiment, and FIG. 1B is a schematic cross-section of FIG. 1A taken in line I-I. As shown in FIG. 1A and FIG. 1B, the measuring container 10 employed in the present exemplary embodiment includes thereinside a plasma generation electrode 20 and a carbon electrode 30, which are the pair of electrodes. The measuring container 10 exhibits a substantially cylindrical shape, having a portion of its side face as if truncated to form a flat face shape. A circular, light-transmissive portion 11 is included in the flat face portion. A light receiver 40 is disposed outside the measuring container 10. The light receiver 40 is disposed to be capable of receiving the luminescence of the analyte heavy metal ions generated by applying a voltage across the plasma generation electrode 20 and carbon electrode 30 through the light-transmissive portion 11. The plasma generation electrode 20 is disposed parallel to a liquid surface 61 of a specimen 60, and a tip end of the plasma generation electrode 20 is disposed so as to abut the light-transmissive portion 11. A portion of a side face of the cylindrical-shaped carbon electrode 30 is disposed to a side face of the measuring container 10 opposing the light-transmissive portion 11, such that the carbon electrode 30 intersects a vertical direction of the measuring container 10 at right angles, and a part of the carbon electrode 30 is exposed to the interior of the measuring container 10. Namely, the length direction of the carbon electrode 30 and the length direction of the plasma generation electrode 20 are at skew-line positions with respect to each other. Most of the surface of the plasma generation electrode 20 is covered by an insulator 22. A portion of the plasma generation electrode 20 that is not covered by the insulator 22 is an exposed region 21 at which a metal wire such as a nichrome wire is exposed.

In the present exemplary embodiment, the exposed region 21 of the plasma generation electrode 20 and the light-transmissive portion 11 contact each other; however, the present exemplary embodiment is not limited thereto, and for example, the plasma generation electrode 20 may be disposed away from the light-transmissive portion 11. The distance between the plasma generation electrode 20 and the light-transmissive portion 11 is not particularly limited, and may, for example, be from 0 cm to 0.5 cm.

The material of the light-transmissive portion 11 is not particularly limited, and may, for example, be set as appropriate according to the wavelength of the luminescence, so long as it is a material that transmits the luminescence generated by applying a voltage across the plasma generation electrode 20 and the carbon electrode 30. Examples of the material of the light-transmissive portion 11 include quartz glass, acrylic resin (PMMA), borosilicate glass, polycarbonate (PC), cyclo-olefin polymer (COP), and polymethylpentene (TPX (registered trademark)). The size of the light-transmissive portion 11 is not particularly limited, so long as it is a size that enables transmission of the luminescence generated by applying the voltage across the plasma generation electrode 20 and the carbon electrode 30.

In the present exemplary embodiment, the measuring container 10 is a bottomed cylindrical shape having a portion of its side face truncated to form the flat face shape running along its length direction; however, the shape of the measuring container 10 is not limited thereto, and may be any desired shape. The material of the measuring container 10 is not particularly limited, and examples include acrylic resin (PMMA), polypropylene (PP), polyethylene (PE), polyvinyl chloride (PVC), polyethylene terephthalate (PET), and polystyrene (PS). In cases in which the measuring container 10 has a bottomed tube shape, the diameter of the measuring container 10 is, for example, from 0.3 cm to 1 cm, and the height of the measuring container 10 is, for example, from 0.9 cm to 5 cm. Into the measuring container 10 is introduced 0.3 $cm^3$ to 0.8 $cm^3$ of the specimen 60.

The light receiver 40 is a part of the known optical measurement instrument referred to in the description of the detection process. The light receiver 40 may be, for example, a transmitter that transmits the luminescence to the optical measurement instrument. Examples of the transmitter include a transmission channel such as an optical fiber.

The method of manufacturing the measuring container 10 is not particularly limited and the measuring container 10 may be a molded body manufactured by injection-molding or the like, or may be manufactured by forming a recess in a substrate such as a plate. The manufacturing method of the measuring container 10 is not particularly limited, and other examples thereof include lithography and machine cutting.

An overview of the plasma spectroscopy analysis method according to the present exemplary embodiment is described for a situation in which the specimen 60 is urine collected from a patient to whom DMSA has been administered and the analyte heavy metal ions are lead ions contained in the specimen 60.

First, as the preliminary addition process, EDTA serving as the auxiliary chelating agent is added to the specimen 60.

Figure 2A:
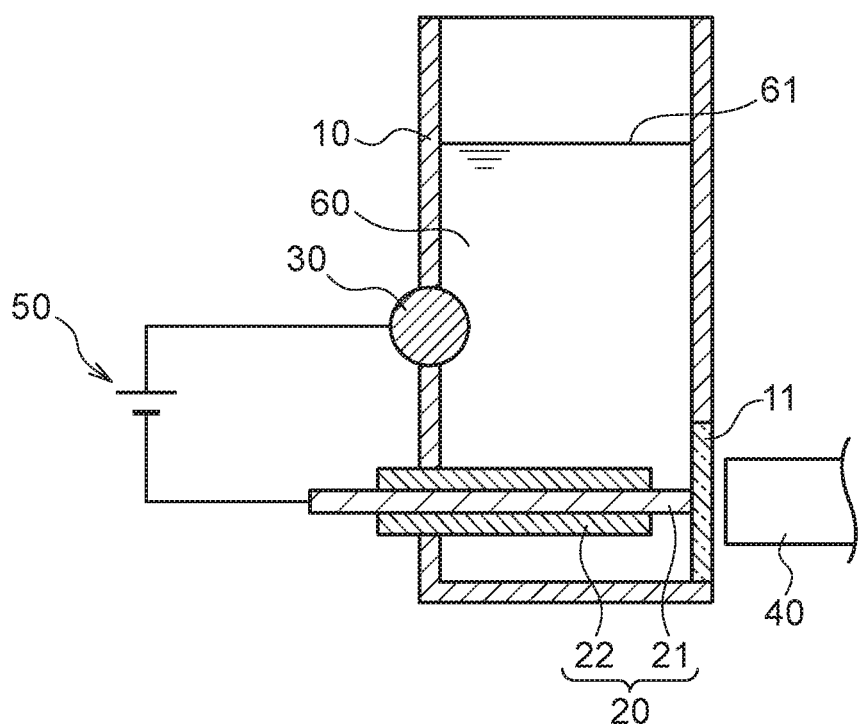
FIG. 2A is a schematic sectional diagram depicting an overview of a concentration process in plasma spectroscopy analysis using the measuring container in FIG. 1A.

As the concentration process, in a state in which the specimen 60 to which the EDTA has been added has been introduced into the measuring container 10, a voltage is applied by a voltage application device 50 such that the plasma generation electrode 20 acts as the cathode and the carbon electrode 30 acts as the anode, as illustrated in FIG. 2A. Accordingly, lead ions in the specimen 60 are attracted to the exposed region 21 of the plasma generation electrode 20 serving as the cathode.

Figure 2B:
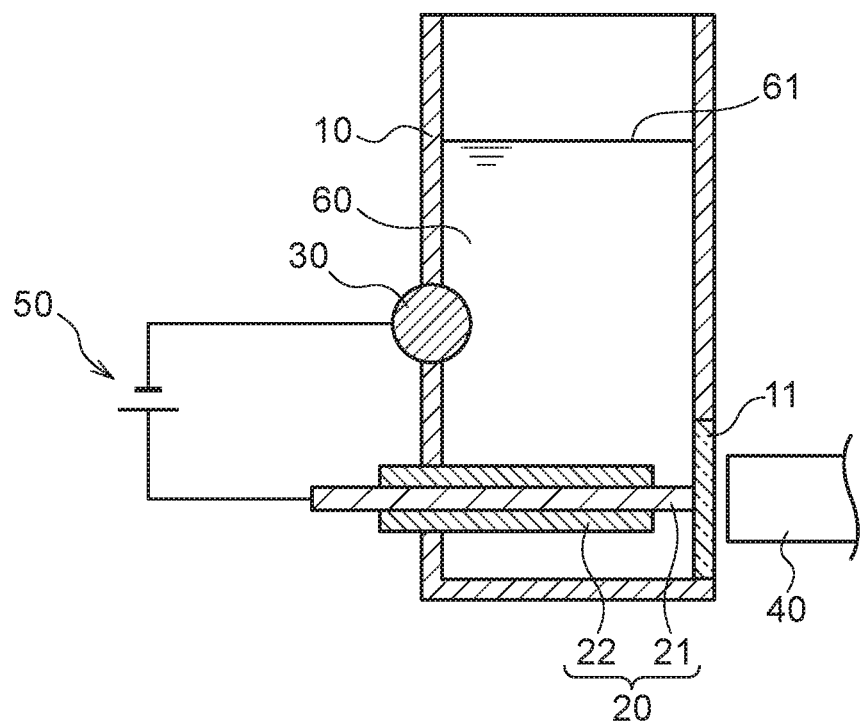
FIG. 2B is a schematic sectional diagram depicting an overview of a detection process in the plasma spectroscopy analysis using the measuring container in FIG. 1A.

Next, as the detection process, a voltage is applied by the voltage application device 50 such that the plasma generation electrode 20 then acts as the anode and the carbon electrode 30 acts as the cathode, as illustrated in FIG. 2B. Accordingly, plasma luminescence is generated from the lead ions that have been attracted around the exposed region 21 of the plasma generation electrode 20 by the prior concentration process, and the light emitted as a result passes through the light-transmissive portion 11 and is received and detected by the light receiver 40.

Figure 3:
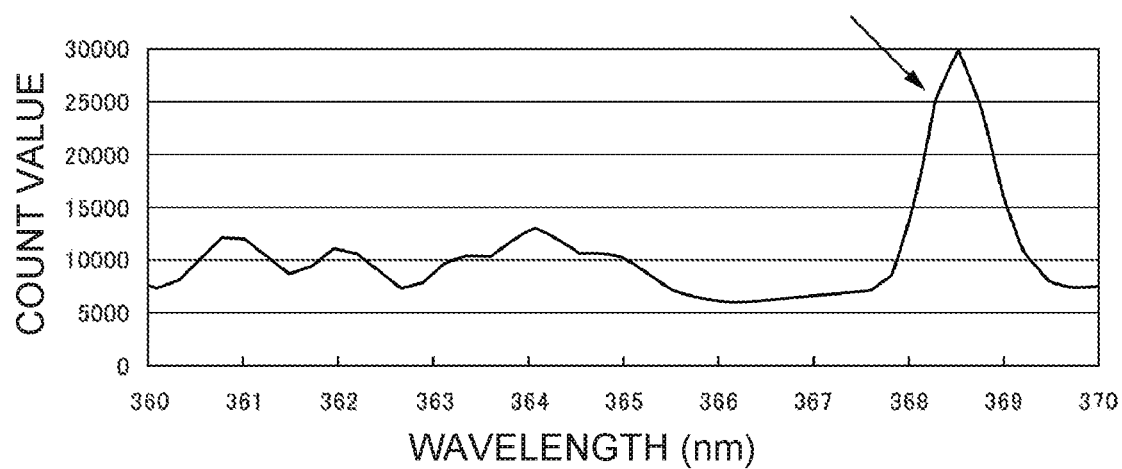
FIG. 3 is a graph illustrating a luminescence spectrum of lead ions according to plasma spectroscopy analysis.

FIG. 3 illustrates a luminescence spectrum of lead ions obtained in the detection process. In this luminescence spectrum, a specific peak of the lead ions is observed in the vicinity of 368.3 nm wavelength, which is marked with an arrow in the graph. The count value of this characteristic peak is used as a peak luminescence amount. A count value of a vicinity from which the specific peak rises (for example, the vicinity of 367 nm wavelength) may be used as a base luminescence amount. Because the base luminescence amount can be regarded as being unrelated to luminescence from the lead ions, the net luminescence amount of the lead ions can be found to serve as the corrected light amount value by dividing the peak luminescence amount by the base luminescence amount. Note that the corrected light amount value may also be found as a value obtained by subtracting the base luminescence amount from the peak luminescence amount.

EXAMPLES

Examples of the present disclosure are described hereinafter. Note that the present invention is not limited by the following Examples.

(1) Plasma Spectrometry Analysis Instrument

The measuring container 10 illustrated in the aforementioned exemplary embodiment was prepared. The plasma generation electrode 20 employed a nichrome wire with a diameter of 0.1 mm, and the length of the exposed region 21 was 0.5 mm. The carbon electrode 30 employed a carbon rod with a diameter of 4.0 mm and a length of 15 mm. The light-transmissive portion 11 employed quartz glass. The plasma generation electrode 20 and carbon electrode 30 were connected to a galvanostat serving as the voltage application device 50. The light receiver 40 employed a single-core optical fiber with a diameter of 400 μm. This optical fiber was connected to a concave grating-type diffractor (prepared in-house).

(2) Specimen

Five capsules containing 100 mg of DMSA were orally administered in one dose to each of seven test subjects. Urine was collected from each of the subjects until six hours after administration, the specimens were all mixed, and the collected urine was used as specimens.

As the preliminary addition process, 5 μL of a 0.5 mol/L EDTA solution (pH 8.0) serving as the auxiliary chelating agent was added to 495 μL of each specimen. Then, lithium hydroxide was dissolved to each specimen to a concentration of 2 mol/L. Hence, the EDTA concentration in the Example specimen was 5 mmol/L. For comparison, Comparative Examples were prepared by adding lithium hydroxide to each specimen to a concentration of 2 mol/L without adding the EDTA solution.

(3) Graphite Furnace Atomic Absorption Spectrometry

Lead ion concentration (unit: ppb) was measured in each specimen by graphite furnace atomic absorption spectrometry (GF/AAS).

(4) Plasma Spectroscopy Analysis

As the concentration process, electricity was supplied to each specimen, using the plasma generation electrode 20 as the cathode and the carbon electrode 30 as the anode under the concentration conditions given below, to concentrate lead ions in the vicinity of the plasma generation electrode 20. The application duration mentioned in the concentration conditions below means a total duration of times in the concentration process in which electricity was supplied and times in which electricity was not supplied. Voltages were applied between the two electrodes to produce the current values given in the concentration conditions below.

Concentration Conditions
Current: 10 mA to 40 mA
Application duration: 1200 seconds
Application switching period: 0.25 μsec
Application switching duty: 50-80%

Directly after the concentration process, as the detection process, electricity was supplied using the plasma generation electrode 20 as the anode and the carbon electrode 30 as the cathode under the plasma generation conditions given below. Peak wavelength amounts (count values) in the vicinity of wavelength 368.3 nm were measured. The application duration mentioned in the plasma generation conditions below means a total duration of times in the detection process in which electricity was supplied and times in which electricity was not supplied. Current was passed between the two electrodes to produce the voltage value given in the plasma generation conditions below.

Plasma Generation Conditions
Voltage: 500 V
Application duration: 2.5 msec
Application switching period: 50 μsec
Application switching duty: 50%

(5) Results

Lead ion measurement results for each specimen according to GF/AAS and plasma spectroscopy analysis as shown above are presented in the following Table 1 and FIG. 4. The GF/AAS values are averages of two measurements for each specimen. The plasma spectroscopy analysis values are presented as corrected light amount values in which peak luminescence amounts are divided by base luminescence amounts.

TABLE 1

| Specimen No. | GF/AAS (ppb) | Plasma spectroscopy analysis | |
| --- | --- | --- | --- |
| | | Comparative Example | Example |
| 1 | 2.99 | 2.58 | 2.30 |
| 2 | 4.34 | 3.41 | 2.58 |
| 3 | 5.15 | 2.59 | 2.21 |
| 4 | 10.63 | 3.24 | 4.22 |
| 5 | 12.87 | 5.15 | 4.38 |
| 6 | 16.01 | 3.10 | 6.35 |
| 7 | 16.25 | 2.54 | 6.01 |

As can be seen from Table 1, the higher the lead ion concentration measured by GF/AAS is, the greater the difference between the lead ion concentration measured by GF/AAS between the corrected light amount value of the Comparative Example is. Therefore, it is clear that lead ions in the Comparative Examples, in which EDTA was not added as an auxiliary chelating agent, could not be measured accurately by the plasma spectroscopy analysis.

In contrast, it can be seen that the increase of light amount values of the Examples, in which EDTA was added as the auxiliary chelating agent, substantially corresponds to the increase of measurement values according to GF/AAS. This is clearly illustrated in FIG. 4, in which the measured values in Table 1 are plotted on graphs.

Figure 4:
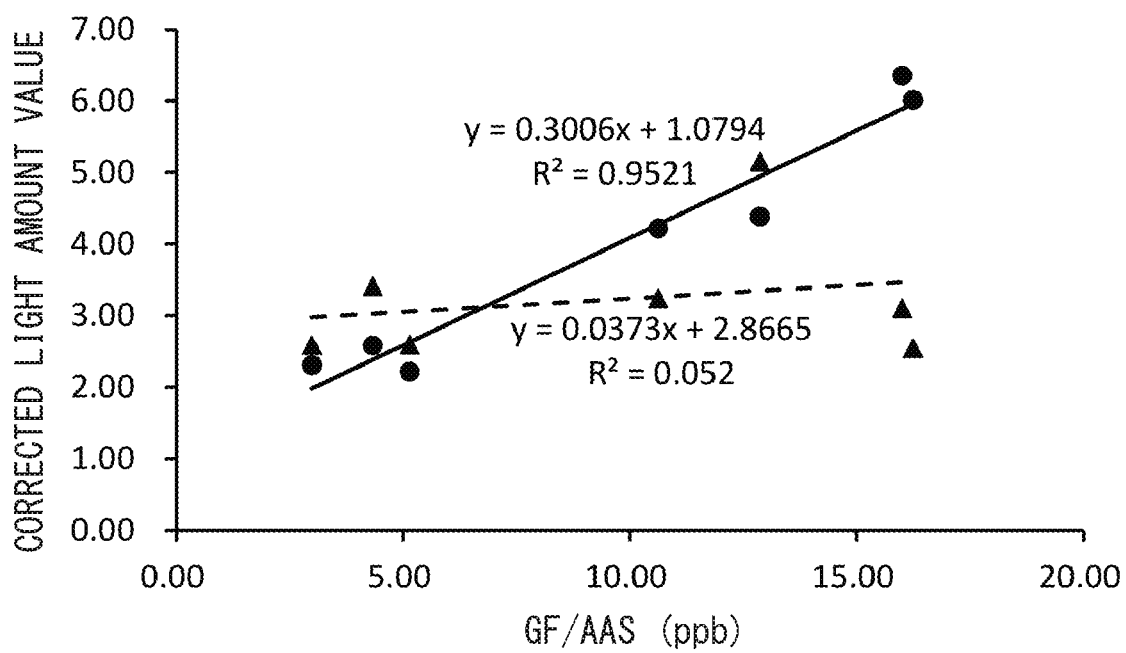
FIG. 4 is a graph illustrating correlations between measurement results of lead ions according to plasma spectroscopy analysis of respective specimens and measurement values according to GF/AAS.

That is, the gradient of a regression line (the broken line in FIG. 4) of the corrected light amount values of the Comparative Examples, represented by triangular marks in FIG. 4, is close to zero. Thus, these values barely at all reflect the increasing lead ion concentrations represented by the measurement values according to GF/AAS. The coefficient of determination ($R^2$) of this regression line is 0.052 and the coefficient of correlation (R), the square root thereof, is 0.2280.

In contrast, the gradient of the regression line (the solid line in FIG. 4) of the corrected light amount values of the Examples, represented by circular marks in FIG. 4, is a rising gradient, confirming that these values reflect increasing lead ion concentrations. The coefficient of determination ($R^2$) of this regression line is 0.9521, and the coefficient of correlation (R), the square root thereof, is 0.9758.

The above confirms that the sensitivity of lead ion concentration measurements by plasma spectroscopy analysis of urine specimens after DMSA administration is dramatically improved by adding EDTA to specimens as an auxiliary chelating agent.

INDUSTRIAL APPLICABILITY

The present invention is applicable to plasma spectroscopy analysis of metal ions, particularly lead ions, using specimens obtained from living bodies. In particular, the present invention is applicable to determining the efficacy of chelation when DMSA is administered.

What is claimed is:

1. A plasma spectroscopy analysis method, comprising:
a preliminary addition process including adding ethylenediaminetetraacetic acid which is capable of bonding with lead ions to a urine specimen collected from a living body, the living body having been orally administered with meso-2,3-dimercaptosuccinic acid before the preliminary addition process;
a concentration process including concentrating the lead ions in the urine specimen at a vicinity of one of a pair of electrodes by applying a first voltage to the pair of electrodes; and
a detection process including generating plasma by applying a second voltage higher than the first voltage to the pair of electrodes, and detecting a luminescence amount of the lead ions caused by the plasma and quantifying the lead ions in the urine specimen based on the luminescence amount of the lead ions.

* * * * *